United States Patent [19]

Ratcliffe et al.

[11] 4,275,207
[45] Jun. 23, 1981

[54] PROCESS FOR PREPARING 7-(1-HYDROXYETHYL)-3-(2-AMINOETHYL-THIO)-1-CARBADETHIACEPH-3-EM-3-CARBOXYLIC ACID AND INTERMEDIATE THEREFOR

[75] Inventors: Ronald W. Ratcliffe, Matawan; Thomas N. Salzmann, North Plainfield, both of N.J.

[73] Assignee: Merck & Co., Inc., Rahway, N.J.

[21] Appl. No.: 67,599

[22] Filed: Aug. 17, 1979

Related U.S. Application Data

[63] Continuation of Ser. No. 933,322, Aug. 14, 1978, abandoned.

[51] Int. Cl.³ .......................................... C07D 471/04
[52] U.S. Cl. ................................ 546/183; 260/239 A
[58] Field of Search ..................... 546/183; 544/16, 17

[56] References Cited

U.S. PATENT DOCUMENTS

| 3,923,796 | 12/1975 | Rapoport | 546/183 |
| 3,950,357 | 4/1976 | Kahan et al. | 424/271 |
| 4,123,528 | 10/1978 | Cama et al. | 424/248.32 |
| 4,150,156 | 4/1979 | Beattie et al. | 544/17 |
| 4,174,316 | 11/1979 | Christensen et al. | 546/183 |

OTHER PUBLICATIONS

Barash et al., Chem. Abst. 1977, vol. 87, No. 135049q & 135050.
Theilheimer, Synthetic Methods of Organic Chemistry, vol. 29, Karger, New York, 1975, No. 465.

Primary Examiner—John M. Ford
Assistant Examiner—Natalia Harkaway
Attorney, Agent, or Firm—James A. Arno; Hesna J. Pfeiffer

[57] ABSTRACT

Disclosed is a process for preparing 7-(1-hydroxethyl)-3-(2-aminoethylthio)-1-carbadethiaceph-3-em-3-carboxylic acid and its pharmaceutically acceptable salts and esters (I) by total synthesis starting with L-aspartic acid and proceeding via intermediate II:

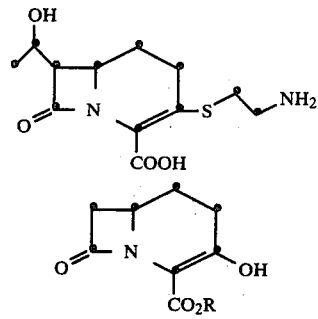

R=blocking group

3 Claims, No Drawings

PROCESS FOR PREPARING 7-(1-HYDROXYETHYL)-3-(2-AMINOETHYLTHIO)-1-CARBADETHIACEPH-3-EM-3-CARBOXYLIC ACID AND INTERMEDIATE THEREFOR

This is a continuation of application Ser. No. 933,322 filed Aug. 14, 1978, now abandoned.

BACKGROUND OF THE INVENTION

This invention relates to a process for preparing 7-(1-hydroxyethyl)-3-(2-aminoethylthio)-1-carbadethiaceph-3-em-3-carboxylic acid and its pharmaceutically acceptable salts and esters (I) which are useful as antibiotics:

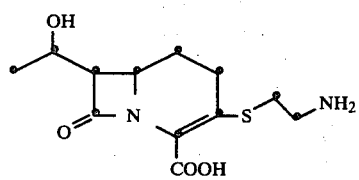

The compound of Structure I might for convenience be called "homothienamycin" on reference to the known antibiotic thienamycin III:

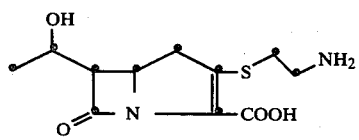

Homothienamycin (I) is disclosed and claimed in copending, commonly assigned U.S. Patent Application Ser. No. 903,455 (filed May 8, 1978) now U.S. Pat. No. 4,150,156 issued Apr. 17, 1979 which is incorporated herein by reference to the extent that it describes I and its utility as an antibiotic. Also incorporated by reference is U.S. Pat. No. 3,950,357 which discloses and claims thienamycin; this patent is incorporated by reference to the extent that it teaches the utility of antibiotics such as III and by analogy I.

The process of the present invention is a total synthesis, starting with L-aspartic acid and proceeding in a stereo-selective manner via intermediate II.

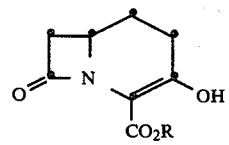

wherein R is a conventional protecting group. The details of the total synthesis are given below.

DETAILED DESCRIPTION OF THE INVENTION

The process of the present invention may conveniently be summarized by the following reaction diagram:

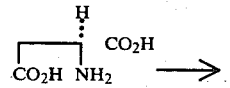

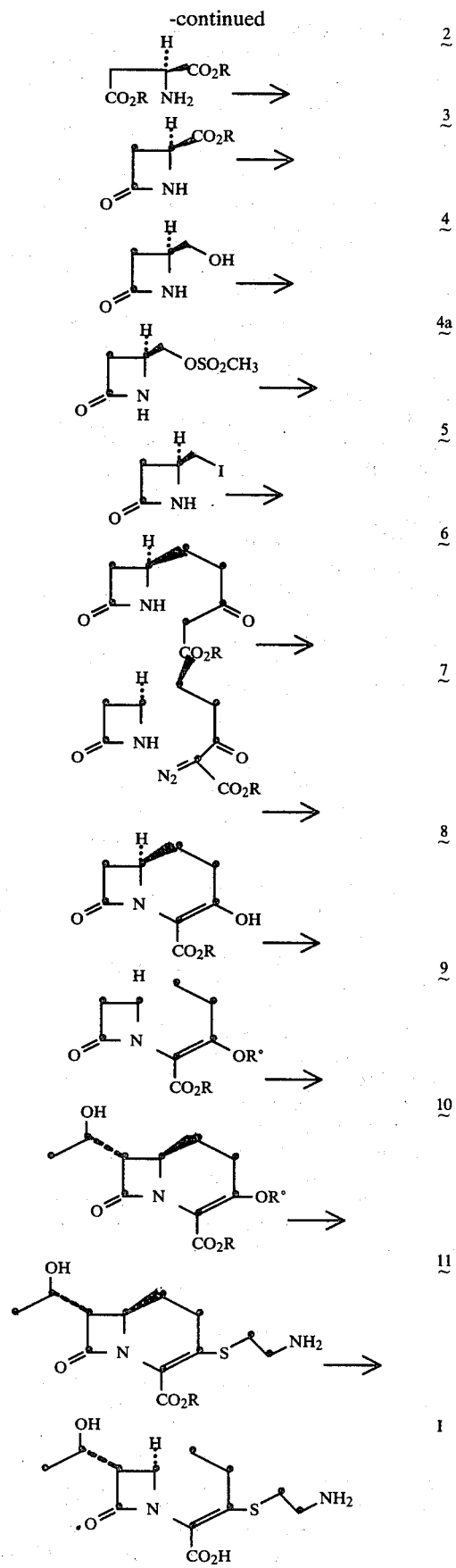

In words relative to the above diagram. L-aspartic acid 1 is esterified according to well known procedures. Typically 1 in a solvent such as benzene, toluene, chloroform or the like is treated with an esterifying agent such as benzyl alcohol, methanol, ethanol, isopropanol, or the like in the presence of p-toluene sulfonate acid, HCl, HBr, or the like at a temperature of from 0° to 110° C. for from 1 to 24 hours to achieve the desired establishment and hence protection of the carboxyl functions. The resulting species 2 in a solvent such as ether, THF, DME or the like is treated with trimethylchlorosilane, or the like followed by treatment with EtMgBr, MeMgI, $\phi$MgBr or the like at a temperature of from −40° to 50° C. for from 1 to 72 hours to provide azetidinone 3. Reduction of species 3 with a reducing agent such as NaBH$_4$, or the like in a solvent such as methanol, ethanol, isopropanol or the like at a temperature of from −10° to 40° C. for from 1 to 6 hours provides 4. (For purposes here, the symbols: Et, Me, $\phi$, and iPr stand for: ethyl, methyl, phenyl and isopropyl, respectively.)

Treatment of 4 in a solvent such as methylene chloride, CHCl$_3$ or the like with methane sulfonyl chloride, methane sulfonic anhydride or the like in the presence of a base such as Et$_3$N, iPr$_2$NEt, or the like followed by treatment with a stoichiometric to 5 fold excess of sodium iodide in acetone yields 5 via 4a.

Treatment of 5 in a solvent such as THF, DME (dimethoxy ethane), ether, or the like with

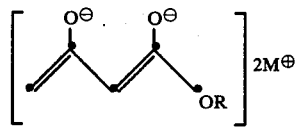

at a temperature of from −78° to 25° C. for from 1 to 24 hours provides 6 wherein M is any compatible counter ion such as lithium, or other alkali metal; R is any conventional carboxyl protecting group such as t-butyl, benzyl, p-methoxybenzyl, or the like.

Diazotization of 6 is accomplished to provide 7 by treating 6 in a solvent such as CH$_3$CN, $\phi$CN ($\phi$=phenyl), or the like at a temperature of from −20° to 25° C. for from 1 to 24 hours with an azide such as p-carboxybenzene sulfonyl azide, tosyl azide, or the like in the presence of a base such as Et$_3$N, iPr$_2$NEt or the like.

Cyclization of 7 to provide 8 is accomplished by treating 7 in a solvent such as benzene, toluene, octane or the like for from 1 to 5 hours at a temperature of from 50° to 110° C. in the presence of a catalyst such as bis-(acetylacetonato)CuII, [Cu(acac)$_2$],

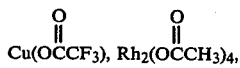

or the like. Intermediate 8 is a mixture of keto-enol tautomers which exists primarily as the shown enol form.

Establishment of leaving group OR° is accomplished by treating intermediate enol 8 with tosyl anhydride, mesylanhydride, tosyl chloride, nosyl chloride, or the like in the presence of a base such as Et$_3$N, iPr$_2$NEt, or the like in a solvent such as CH$_2$Cl$_2$, CHCl$_3$, or the like at a temperature of from −30° to 25° C. for from 0.5 to 10 hours; thus relative to intermediate species 9 R° may for example be Ts(tosyl), CH$_3$SO$_2$—,

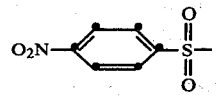

or the like.

Alkylation of 9 provides 10 on treating 9 in a solvent such as THF, DME, ether or the like with a strong base such as lithium diisopropylamide (LDA) Li-tetramethylpiperidide, KH or the like followed by treatment with a stoichiometric to 20 fold excess of acetaldehyde. Typically the reaction is conducted at a temperature of from −78° to 25° C.; and typically the acetaldehyde is added after 5 to 60 minutes after addition of the strong base; the alkylation reaction is completed in 0.1 to 1 hours. The aldol reaction provides a mixture of isomers which is conveniently separated by chromatography.

The aminoethylthio side chain is established by treating 11 in a solvent such as DMF, HMPA, DMSO or the like at a temperature of from −40° to 50° C. for from 1 to 72 hours with aminoethyl mercaptan or an acid addition salt in the presence of a base such as Et$_3$N, iPr$_2$NEt, pyridine or the like.

Deblocking of 11 provides I. Typically the deblocking is accomplished by hydrolysis or hydrogenation. When R is t-butyl, p-methoxybenzyl, benzhydryl or the like acid hydrolysis at a temperature of from 0° to 25° C. for from 0.1 to 5 hours is appropriate; when the carboxyl protecting group R is p-nitro benzyl, benzyl, or the like hydrogenation in a solvent such as dioxane, ethanol, or the like in the presence of a catalyst such as Pd/C, or the like under a hydrogen pressure of from 1 to 40 atmospheres for from 0.2 to 4 hours is appropriate.

The following Example illustrates but does not limit the process of the present invention. All temperatures are expressed in °C.

EXAMPLE 1

Preparation of Homothienamycin

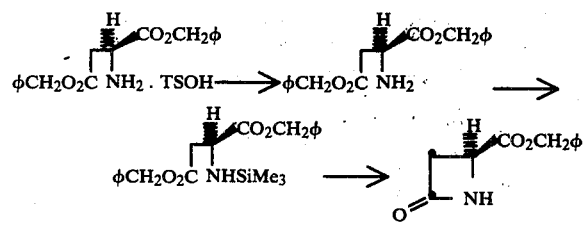

Benzyl (S)-azetidin-2-one-4-carboxylate

To a 1000 ml separatory funnel are added dibenzyl (S)-aspartate p-toluenesulfonic acid salt (48.6 g, 0.1 mole), ice-cold diethyl ether (300 ml), ice-cold water (100 ml), and ice-cold saturated aqueous potassium carbonate (50 ml). The mixture is shaken vigorously and the layers are separated. The aqueous portion is extracted with more cold diethyl ether (2×100 ml). The combined ether solution is washed with brine, dried with magnesium sulfate, and evaporated under vacuum to provide dibenzyl (S)-aspartate (31.4 g, 0.1 mole) as a colorless liquid.

The dibenzyl (S)-aspartate in anhydrous diethyl ether (200 ml) is cooled in an ice-bath under a nitrogen atmosphere. Trimethylchlorosilane (12.7 ml, 0.1 mole) is added to the stirred solution to give a white precipitate. Triethylamine (14.0 ml, 0.1 mole) is then added to the mixture. The cooling bath is removed and the mixture is stirred at room temperature (25° C.) for 2 hrs. The mixture is then filtered directly into a 3-neck, 1-liter, round bottom flask fitted with a sintered glass funnel, magnetic stirrer, and a vacuum-nitrogen inlet. This operation is carried out under a blanket of nitrogen, care being taken to exclude atmospheric moisture. The sintered glass funnel is replaced by a stopper and the ether is evaporated under vacuum with stirring to provide dibenzyl (S)-N-trimethylsilylaspartate (35.5 g, 0.092 mole) as a slightly hazy oil.

Anhydrous diethyl ether (250 ml) is added to the flask containing the silyl derivative and the magnetic stirrer is replaced by a mechanical stirrer. The resulting solution is stirred under a nitrogen atmosphere with ice-bath cooling. Ethereal ethyl magnesium bromide (34 ml of a 2.94 M solution, 0.1 mole) is added dropwise over 40 min. to give a cream colored, stirable precipitate. The cooling bath is removed and the mixture is stirred at room temperature. After ca 1.5 hrs, an unstirable, viscous gum forms. The mixture is allowed to stand overnight at room temperature. The mixture is then cooled in an ice-methanol bath while ammonium chloride saturated 2 N hydrochloric acid (100 ml) is added slowly with stirring. The resulting mixture is diluted with ethyl acetate (100 ml) and water (100 ml) and the layers are separated. The aqueous portion is extracted with more ethyl acetate (3×100 ml). The combined organic solution is washed with water (200 ml), 5% aqueous sodium bicarbonate solution (100 ml), water (100 ml), and brine, dried with magnesium sulfate, and filtered. Evaporation of the solvent under vacuum gives an orange oil interspersed with a fine, granular precipitate (25.3 g). This material is dissolved in warm chloroform (75 ml), diluted with petroleum ether (125 ml), seeded, scratched, and cooled in an ice-bath. The precipitate is collected, washed with petroleum ether, and dried under vacuum to give benzyl (S)-azetidin-2-one-4-carboxylate (3.85 g) as an off-white solid mp 136°-139° C. The mother liquors are combined, diluted with petroleum ether to 500 ml, seeded, and left in a refrigerator for several days. The resulting precipitate is collected, washed with petroleum ether, and dried under vacuum to give additional product (0.82 g) as pale yellow crystals. Recrystallization of a sample from chloroform-petroleum ether gave the product as small, white flakes: mp 141°-143°; $[\alpha]_D = -43.4°$ (c3.275 in CHCl$_3$); IR(CHCl$_3$) 3425, 1778, 1746 cm$^{-1}$; $^1$H NMR (CDCl$_3$) δ3.00 (ddd, 1,J=1.9, 3.2, and 14.6 Hz, H-3a), δ3.35 (ddd, 1, J=1.5, 5.4, and 14.6 Hz, H-3b), δ4.20 (dd, 1, J=3.2 and 5.4 Hz, H-4), δ5.22 (s, 2, OCH$_2$Ph), δ6.48 (m, 1, NH), 7.38 (s, 5, phenyl); mass spectrum m/e 205 (M+), 163, 91, 70, 43.

Anal. Calcd. for C$_{11}$H$_{11}$NO$_3$: C, 64.38; H, 5.40; N, 6.83. Found: C, 64.10; H, 5.70; N, 6.77.

STEP B

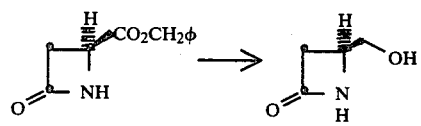

4(S)-4-Hydroxymethylazetidin-2-one

Sodium borohydride (3.69 g, 97.5 mmol) is added in one portion to a suspension of benzyl 4(S)-azetidin-2-one-4-carboxylate (20.0 g, 97.5 mmol) in 300 ml of absolute methanol at 0° C. The mixture is then allowed to warm slowly with periodic cooling being supplied to keep the internal temperature <30° C. After stirring for 2 hr., glacial acetic acid (23.4 g, 390 mmol) is added and the reaction mixture is concentrated under vacuum. The residue is treated with 500 ml of chloroform and filtered. The filtrate is concentrated under vacuum and the residue is chromatographed on 250 g of silica gel (4:1, chloroform: methanol) to yield 9.62 g (98%) of 4(S)-hydroxymethylazetidin-2-one as a white solid: m.p. 51°-53° C.; $[\alpha]_D = +68.0°$ (C=2.676 in CHCl$_3$; IR (CHCl$_3$) 3410, 1765 cm$^{-1}$ 1H NMR (CDCl$_3$) δ7.07 (1H, br. s, NH), δ4.05 (1H, br. s, OH), δ3.77 (2H, m H4, H-5a or b), δ3.58 (1H, dd, J=11, 6, H-5a or b), δ2.97 (1H, ddd, J=14.5, 4.8, 1.3, H3b), δ2.7 (1H, br. d, J=14.5, H3a); mass spectrum m/e 101 (M+), 83.

STEP C

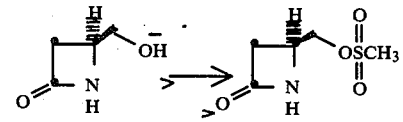

4(S)-4-Methanesulfonyloxymethyl azetidin-2-one

Methane sulfonyl chloride (11.46 g, 100 mmol) is added dropwise by syringe to a solution of 4(S)-4-hydroxymethyl azetidin-2-one (10.1 g, 100 mmol) and triethyl amine (10.1 g, 100 mmol) in 15 ml of dry methylene chloride at 0° C. (Warming is necessary in order to initially solubilize the alcohol. The resulting solution is then cooled to 0° C. prior to addition of the other reagents). The resulting solution is stirred at 0° C. for 1 hr. during which time a voluminous precipitate is produced. At the end of this time, the reaction mixture is filtered and the filtrate is concentrated under vacuum. The two solid residues are combined and treated with 500 ml of chloroform. The resulting mixture is filtered to yield substantially pure 4(S)-4-methanesulfonyloxymethyl azetidin-2-one as a white solid. The filtrate, which contains most of the triethylamine hydrochloride, is concentrated under vacuum and chromatographed on 200 g of silica gel (4:1 chloroform:methanol) to yield an additional quantity of mesylate. This material is combined with that obtained previously and recrystallized from chloroform to yield 15.57 g (87%) of 4(S)-4-methanesulfonyloxymethylazetidin-2-one as colorless needles: m.p. 109.5°-110.5° C.; $[\alpha]_D = +25.8°$ (C=1.025 in H$_2$O);

NMR (D$_2$O) δ 4.62 (1H, dd, J=11.2, 3.0, H-5a or b), δ 4.43 (1H, dd, J=11.2, 6, H-5a or b), δ 4.12 (1H, m, H4) δ 3.26 (3H, s

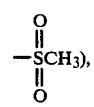

δ 3.19 (1H, dd, J=15, 4.5, H3b).

δ 2.88 (1H, dd, J=15, 2.5, H3a); mass spectrum m/e 179 (M+), 136;

Anal: Calc: C, 33.51; H, 5.06; N, 7.82; S, 17.89.
Found: C, 33.54; H, 5.08; N, 7.72; S, 17.93.

STEP D

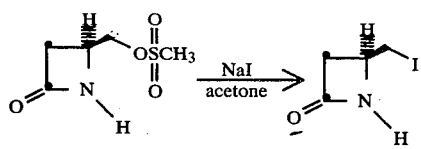

4(S)-4-Iodomethylazetidin-2-one

A mixture of 4(S)-4-methanesulfonyloxy azetidin 2-one (11.8 g, 65.9 mmol) and powdered sodium iodide (19.8 g, 132 mmol) in 130 ml of acetone is heated at reflux for 6 hr. The resulting reaction mixture is concentrated in vacuo, treated with 200 ml of chloroform and filtered. The filtrate is washed with 2×50 ml of water and dried over magnesium sulfate. The organic phase is filtered, concentrated in vacuo, and chromatographed on 250 g of silica gel (ethyl acetate) to yield 11.94 g (86%) of 4(S)-4-iodomethyl-azetidin-2-one as a white solid. This material is recrystallized from ether-petroleum ether to yield white crystals: mp 91°–92° C.; $[\alpha]_D = -23.7°$ (C=1.354 in $CHCl_3$); IR ($CHCl_3$) 3450, 1765 cm$^{-1}$; 1H NMR ($CHCl_3$) δ 6.13 (brs, N-H), δ 3.94 (m, 1H, Hc), δ 3.36 (m, 2H, Hd and e), δ 3.16 (ddd, 1H, J=14.9, 5.4, 2.3, Ha), δ 2.72 (d, d, d, 1H, J=14.9, 2.1, 2, Hb) mass spectrum m/e 211 (M+), 168, 142, 127, 84.

STEP E

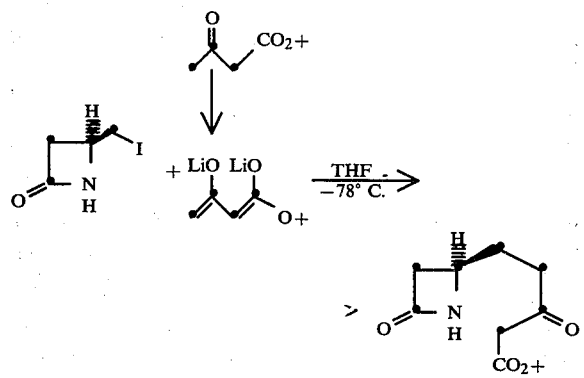

4(R)-4-[4-(t-butyloxycarbonyl)-3-oxobutyl]-azetidin-2-one n Butyl lithium (15.3 ml of 2.6 M solution in hexane, 39.8 mmol) is added by syringe to a solution of diisopropylamine (4.028 g, 39.8 mmol) in 70 ml of freshly distilled tetrahydrofuran (Nabenzophenone) at 0° C. The resulting solution is stirred at 0° C. for 15 min. prior to the dropwise addition of tert butyl acetoacetate (3.148 g, 19.9 mmol). The resulting yellow orange solution is stirred at 0° C. for 20 min. To this solution is added a solution of 4(S)-4-iodomethyl-azetidin-2-one (2.00 g, 9.48 mmol) in 6 ml of tetrahydrofuran. After stirring at 0° C. for 1.25 hr, 10 ml of saturated aqueous ammonium chloride solution is added and the mixture is poured into a separatory funnel containing ethyl acetate (100 ml) and 2% aqueous hydrochloric acid solution (50 ml). The organic phase is separated, washed with water (50 ml) and brine (30 ml) and dried over magnesium sulfate. The solvent is evaporated under vacuum and the residue is chromatographed on 50 g of silica gel with ethyl acetate elution to yield 500 mg (25% recovered of 4(S)-4-iodomethylazetidin-2-one and 1.44 g (84% based on recovered starting material) of 4(R)-4-[4-(t-butyloxycarbonyl)-3-oxobutyl]azetidin 2-one as a white solid. Recrystallization from ether-petroleum ether give white flakes: m.p. 63°–64° C.; $[\alpha]_D + 2.90°$ (C=4.41 in $CHCl_3$), IR ($CHCl_3$) 3380, 1750, 1705 cm$^{-1}$; 1H NMR ($CDCl_3$) δ 6.02 (1H, br.s, —N—H), δ 3.7 (1H, m, H-4), δ 3.36 (2H, s

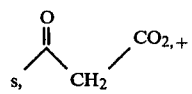

δ 3.08 (1H, ddd, J=15, 5, 2.5, H-3b), δ 2.6 (3H, m, H-3a 2H-6), δ 2.95 (2H, m, 2H-5); mass spectrum m/e 241 (M+), 185, 168, 126

Anal. Calc: C, 59.73; H, 7.94; N, 5.81. Found: C, 59.74; H, 8.12; N, 5.87.

STEP F

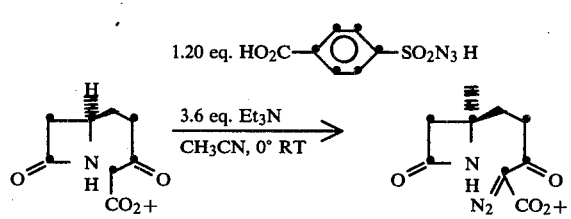

4(R)-4-[4-t-butyloxycarbonyl)-4-diazo-3-oxobutyl]azetidin-2-one

Triethylamine (3.37 g, 33.3 mmol) is added by syringe to a mixture of 4(R)-4-[4-(t-butyloxycarbonyl)-3-oxobutyl]azetidin-2-one (2.22 g, 9.24 mmol) and p-carboxybenzenesulfonylazide (2.52 g, 11.1 mmol) in 75 ml of dry acetonitrile at 0° C. When the addition is complete, the reaction is allowed to warm to R.T. and stirred overnight. The reaction mixture is then diluted with 300 ml of ether and filtered. Concentration of the filtrate in vacuo yields a yellow oil which is chromatographed on 100 g of silica gel (ethyl acetate) to give 2.30 g (93%) of 4(R)-4-[4-t-butyloxycarbonyl)-4-diazo-3-oxobutyl]azetidin-2-one as a colorless oil. This material is triturated with petroleum ether to yield an off-white solid. IR($CHCl_3$) 3415, 2118, 1755, 1704, 1649 cm$^{-1}$; 1H NMR ($CDCl_3$) δ 6.64 (br.s, 1H, N-H), δ 3.63 (m, 1H, Hc), δ 3.02 (ddd, J=16, 5, 2 1H, H$_b$) δ 2.9 (m, 2H, Hfg) δ 2.55 (ddd, J=16, 2, 1.5, 1H, Ha), δ 1.9 (m, 2H, Hde), δ 1.55 (s, 9H, tBu)

STEP G

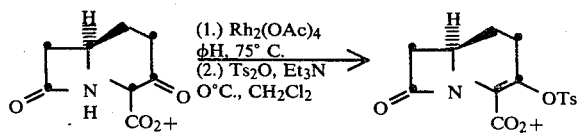

Tert-Butyl 6(R)-3-p-toluenesulfonyloxy-8-Oxo-1-Azabicyclo[4,2,0]oct-2-ene-2-carboxylate A mixture of 4(R)-4-[4-(t-butyloxycarbonyl)-4-diazo-3-oxobutyl]azetidin-2-one (1.75 g, 6.55 mmol) and rhodium (II) acetate (17 mg) in 130 ml of degassed benzene is heated at 75°-80° C. until t.l.c. analysis (ethyl acetate) shows no remaining starting material. The mixture is cooled to room temperature, filtered, and concentrated in vacuo to yield tert-butyl 6(R), 3-hydroxy-8-oxo-1-azabicyclo[4.2.0]oct-2-ene-2-carboxylate.

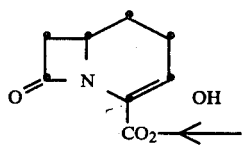

This material is redissolved in 35 ml of dry methylene chloride and cooled to 0° C. prior to the successive addition of p-toluenesulfonic anhydride (2.56 g, 7.86 mmol) and triethylamine (795 mg. 7.86 mmol). The resulting solution is stirred at 0° C. for 45 min., then diluted with ethyl acetate and washed with 2% aqueous hydrochloric acid solution, water and brine and dried over anhydrous magnesium sulfate. The solvent is removed in vacuo to give a viscous oil which is chromatographed on 100 g of silica gel (ether) to yield a white solid. This material is recrystallized from ether-petroleum ether to yield 1.79 g (70%) of tert butyl 6(R)-3-p-toluenesulfonyloxy-8-oxo-1-azabicyclo[4,2,0]oct-2-ene-2-carboxylate as white flakes: m.p. 99°-100° C.; $[\alpha]_D = +132.5°$ (C=3.57, CHCl$_3$); I.R. (CHCl$_3$) 1772, 1725, 1600, 1155, H NMR (CDCl$_3$) δ 7.61 (AA' BB', 4H, aromatic), δ 3.64 (m, 1H, H6), δ 3.28 (dd, J=15.2, 5, 1H, H7b), δ 2.64 (dd, J=15.2 2.3, 1H, H7a), δ 2.4-2.55 (m, 1H, H4a or b), δ 2.45 (s, 3H,

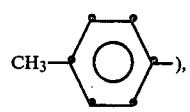

δ 2.23 (m, 1H, H4a or b), δ 1.3-1.7 (m, 2H, H5a & b), δ 1.49 (s, 9H,tBu); mass spectrum m/e 393(M+), 337, 320, 292, 238, 182, 155.

Anal calcd for C$_{19}$H$_{23}$NO$_6$S: C, 58.00; H, 5.89; N, 3.56; S, 8.15. Found: C, 57.98; H, 5.99; N, 3.34; S, 7.80.

STEP H

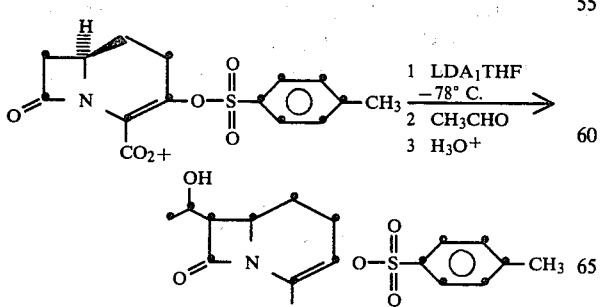

Tert Butyl 6(R), 7(S)-3-p-toluenesulfonyloxy-7-[1-(R)hydroxyethyl]-8-oxo-1-azabicyclo[4.2.0]oct-2-ene-2-carboxylate (trans-R isomer)

Butyl lithium (960 μl of a 2.3 M solution, 2.2 mmol) is added by syringe to a solution of diisopropyl amine (223 mg, 2.2 mmol) in 20 ml of freshly distilled tetrahydrofuran at −78° C. The resulting solution is stirred at −78° C. for 15 min. prior to the dropwise addition of a solution of tert-butyl 6(R)-3-p-toluenesulfonyloxy-8-oxo-1-azabicyclo[4.2.0]oct-2-ene-2-carboxylate (786 mg, 2.0 mmol) in 2 ml of tetrahydrofuran. The resulting dark orange enolate solution is stirred at −78° C. for 15 min. prior to the addition of acetaldehyde (880 mg, 20 mmol). After an additional 10 min. at −78° C., saturated aqueous ammonium chloride solution is added and the mixture is allowed to warm to room temperature. The reaction mixture is diluted with ethyl acetate (100 ml) and washed with 2% aqueous hydrochloric acid solution, water and brine and dried over anhydrous magnesium sulfate. Removal of the solvents in vacuo gives an oil which is chromatographed on 20 g of silica gel (ethyl ether) to remove polar and non-polar by-products. The product mixture is isolated as a white foam (537 mg). Starting material (37 mg, 5%) is also isolated as a white solid. The product mixture is chromatographed on three 2000μ silica gel GF plates (ether, 4 elutions). The most polar compound is S-trans (277 mg); the intermediate is R-trans (173 mg) and the least polar is a mixture of R and S-cis (80 mg). The total yield based on recovered starting material is 63%. Yield of the desired trans-R is 21%. IR (CHCl$_3$) 1763, 1724 cm$^{-1}$; NMR (CDCl$_3$) δ 7.62 (AA' BB', 4H, aromatic), δ 4.20 (m, 1H, H8), δ 3.62 (ddd, J=11, 2.1, 2, 1H, H-6), δ 2.87 (dd, J=6.5, 2.1, 1H, H-7), δ 2.46 (s, 3H, CH$_3$-Ar), δ 2.2-2.4 (m, 2H, H4a & b), δ 1.3-1.7 (m, 2H, H5a & b), δ 1.48 (S, 9H, tBu), δ 1.33 (d, J=6.5,

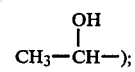

mass spectrum (m/e) 437 (M+), 381, 364, 336, 282, 226, 182.

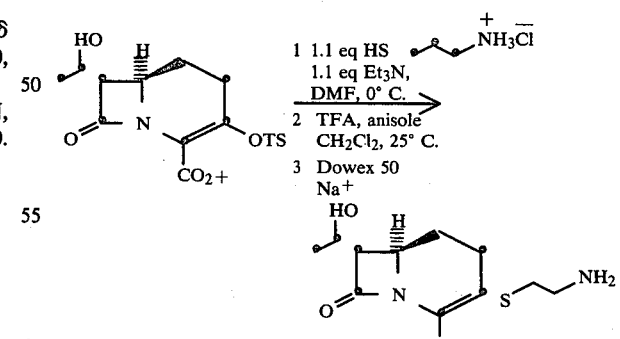

Homothienamycin

Triethylamine (23.3 mg, 0.23 mmol) is added by syringe to a mixture of tert-butyl 6(R), 7(S)-3-p-toluenesulfonyloxy-1-[1-(R)-hydroxyethyl]-8-oxo-1-azabicyclo[4.2.0]oct-2-ene-2-carboxylate (91 mg, 0.208 mmol) and cysteamine hydrochloride (26 mg, 0.23 mmol) in 600 μl of dry dimethylformamide at 0° C. The resulting mixture is stirred at 0° C. for 5 hr, then concentrated under high vacuum. The residue is partitioned between methylene chloride and saturated aqueous potassium carbonate in a separatory funnel and the organic phase is separated. The aqueous phase is washed with an additional portion of methylene chloride and the combined organic phases are washed with saturated aqueous sodium chloride solution and dried over anhydrous magneisum sulfate. Removal of the solvent in vacuo gives 56 mg (79%) of crude tert-butyl 6(R), 7(S)-3-(2-aminoethylthio)-1-[1-(R)-hydroxyethyl]-8-oxo-1-azabicyclo[4.2.0]oct-2-ene-2-carboxylate. IR(CHCl$_3$) 1750, 1700, 1600 cm$^{-1}$; UV (MeOH) λ max=295. This material is dissolved in 500 ml of methylene chloride and 500 μl of anisole. Trifluoroacetic acid (500 μl) is added and the resulting solution is stirred at room temperature with periodic monitoring by tlc (4:1 chloroform-methanol). After 1 hr, no starting material remains. The volatiles are removed under high vacuum and the residue is dissolved in 1 ml of 0.1 M pH 7 phosphate buffer. This solution is applied to a column of Dowex 50 resin -Na+ cycle (40 ml) and eluted with deionized water with 6 ml fractions being collected. Fractions 10-20 are combined. UV analysis shows λ max=279. Assuming E=8000, 20 mg (34%) of product is produced. This solution is divided into two approximately equal volumes. One portion is lyophilized to give 12 mg homothienamycin as an off-white solid. Analysis of this material by HPLC (C$_{18}$ Bondapak Reverse Phase, 37-75μ, 10% aq THF) showed 90% purity). NMR (D$_2$O) δ 4.26 (ps. p, J=6.5, H-8), δ 3.70 (ddd, J=11,2,2, 1H, H-6), δ 3.18 (dd, J=6.5, 2, 1H, H-7), δ 3.0-3.3 (m, 2H, H$_3$N-C$\underline{H}_2$—), δ 2.8-3.2 (m, 2H, —S C$\underline{H}_2$—), δ 2.3-2.6 (m, 3H, H-4a and b, H5a), δ 1.7 (m, 1H H5b), δ 1.29 (d, J=6.5, 3H,

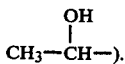

What is claimed is:

1. A process for preparing a compound having the structure:

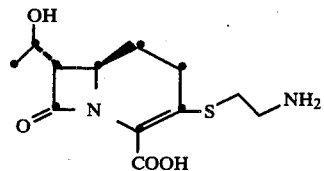

which comprises the steps of cyclizing:

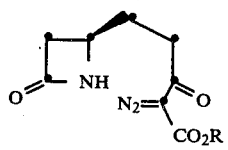

in the presence of a catalyst selected from: bis-(acetylacetonato)Cu,

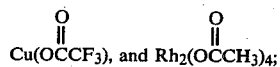

to form:

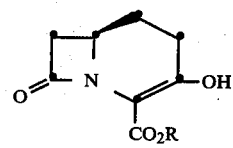

followed by esterifying to form:

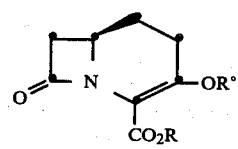

followed by alkylating in the presence of base with acetaldehyde to form:

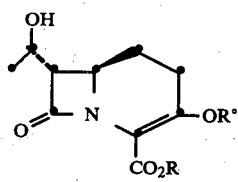

followed by treating with aminoethylmercaptan and deblocking wherein R is a readily removable carboxyl blocking group selected from the group consisting of t-butyl, p-methoxybenzyl, benzhydryl, p-nitrobenzyl, and p-methoxybenzyl and R° is a leaving group selected from the group consisting of tosyl, mesyl, or nosyl.

2. A compound having the structure:

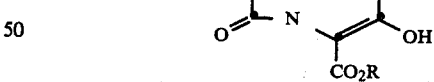

wherein R is a blocking group selected from the group consisting of t-butyl, p-methoxybenzyl, benzhydryl, p-nitrobenzyl, and p-nitrobenzyl.

3. A process for preparing a compound having the structure:

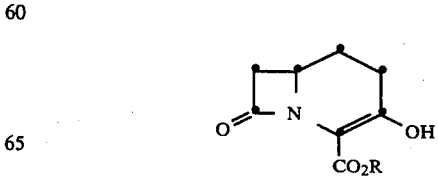

which comprises cyclizing:

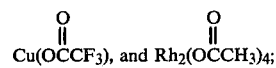
in the presence of a catalyst selected from: bis-(acetylacetonato)Cu,
$$Cu(O\overset{O}{\overset{\|}{C}}CF_3), \text{ and } Rh_2(O\overset{O}{\overset{\|}{C}}CH_3)_4;$$
wherein R is a readily removable carboxyl blocking group selected from the group consisting of t-butyl, p-methoxybenzyl, benzhydryl, p-nitrobenzyl, and p-nitrobenzyl.
* * * * *